United States Patent [19]
Kiefer

[11] Patent Number: 5,259,555
[45] Date of Patent: Nov. 9, 1993

[54] WOODEN AIR FRESHENER WITH FRAGRANCE LOADING CHAMBER

[76] Inventor: Bruce C. Kiefer, 21721 Olson Rd., Franksville, Wis. 53126

[21] Appl. No.: 919,451

[22] Filed: Jul. 27, 1992

[51] Int. Cl.$^5$ .................................................. A61L 9/12
[52] U.S. Cl. ........................................ 239/35; 239/54
[58] Field of Search .............. 239/34, 35, 53, 54, 239/60

[56] References Cited

U.S. PATENT DOCUMENTS

| | | | |
|---|---|---|---|
| 644,158 | 2/1900 | Blake | 239/54 X |
| 1,174,463 | 3/1916 | Zeller | 239/54 |
| 1,866,658 | 7/1932 | Lichtig | 239/54 X |
| 2,218,037 | 10/1940 | Duers et al. | 299/54 |
| 2,241,167 | 5/1941 | Storck | 299/54 |
| 2,416,537 | 2/1947 | Neiser | 131/171 |
| 2,980,102 | 4/1961 | Vaughn | 239/54 X |
| 4,768,686 | 9/1988 | Storti | 239/60 X |
| 4,860,953 | 8/1989 | Hsien | 239/47 |
| 4,889,285 | 12/1989 | Locko | 239/34 |
| 4,915,301 | 4/1990 | Munteanu | 239/45 |

Primary Examiner—Andres Kashnikow
Assistant Examiner—Lesley D. Morris
Attorney, Agent, or Firm—Jansson & Shupe, Ltd.

[57] ABSTRACT

A wooden, refillable container having an interior fragrance loading chamber at the base is filled with air freshening oil. A closure is secured to the bottom of the container to hold the oil inside the chamber, to allow removal for charging and recharging, and to protect the surface on which the container is from contact with the oil. The oil migrates through the wood along the capillaries of the wood grain until it reaches the outside wooden surface of the container. After exposure to the open air, the oil vaporizes, thereby releasing the fragrance into the air. The wood acts as a metering device for the gradual release of the air freshening agent. As the oil evaporates, the wooden member loses its luster and lightens in appearance, signaling that more air freshening agent is needed. This change in appearance allows an observer to easily determine whether the chamber needs to be refilled.

20 Claims, 4 Drawing Sheets

WOODEN AIR FRESHENER WITH FRAGRANCE LOADING CHAMBER

FIELD OF THE INVENTION

This invention is related generally to air fresheners and, more particularly, to refillable air fresheners having a fragrance loading chamber.

BACKGROUND OF THE INVENTION

Air fresheners come in a variety of types. Sprays which release the fragrance in gaseous form provide a quick result, but the effect is not enduring because the fragrance vapors quickly dissipate. Consequently, frequent reapplication is necessary.

To overcome this problem, devices have been introduced which provide for the constant or intermittent emission of fragrance. One means of accomplishing gradual emission of an air freshening scent is to expose the fragrance in semi-solid or liquid form to the atmosphere, resulting in gradual vaporization of the solid or liquid material. This vaporization process may be accelerated by the use of heat.

Desirable characteristics of any air freshening device designed for gradual emission include an attractive physical appearance and an even rate of discharge of the fragrance, so that the scent is neither overpowering nor absent at any time. Ideally, the device should dispense the fragrance at a substantially constant rate over the useful life of the product.

Another beneficial feature of an ideal air freshener would include a container that could be refilled with fragrance so that reuse would be possible instead of disposal. Additionally, the container should be able to adequately hold and contain the air freshening agent and thereby prevent contact with, and potential damage to, surrounding surfaces. Another positive attribute would be low cost to the consumer over the life of the product. An ideal reusable air freshener should also have a method of clearly indicating to the user when more air freshener is needed.

Plastic disposable air fresheners have traditionally dominated the market for continuous-action air freshening devices. The advantage of plastic dispensers is that they are inexpensive to manufacture and package and are consequently less costly in initial cash outlay to the consumer. Because of such low initial cost, such dispensers are generally designed to be replaced rather than refilled when the freshening agent has completely vaporized.

A distinct disadvantage of plastic containers is that such containers are not generally reusable since many of these containers are not designed to be refillable. This disposable aspect of plastic air fresheners raises certain environmental concerns, since many plastics are not biodegradable and must take up valuable landfill space.

Furthermore, such products, because they tend to be inexpensively made, may not be particularly attractive in appearance. The plastic container also does not serve a purpose in the task of accomplishing air freshening, other than to act as a mere container to hold the fragrance agent. An additional disadvantage is that most of these containers have openings in the plastic to allow for the emission of vapors from the container, making accidental contact between the fragrance agent and a surface material more likely. Such contact could cause permanent damage to a table surface or to clothing.

Wooden containers providing for the emission of vapors having an insect repellent purpose are disclosed by the prior art. U.S. Pat. No. 2,218,037 (Duers) teaches the use of a small cedar device into which is inserted a fabric plug soaked in insect repellent and held in place in the interior of the device by a wooden plug. The Duers device is then covered with a permeable coating such as paraffin, which serves to meter the emission of insect repellent vapors. Alternatively, the interior is filled with a paraffin-repellent plug, the paraffin again serving a metering function. In both forms, the Duers patent teaches that the interior of the device holds the repellent during the period of emission from the device. The device is designed to be used where fabric materials are stored to prevent insect damage to clothing. There is no teaching with respect to air freshening dispensers, and no teaching of the use of wood for holding/metering purposes.

The prior art also discloses that oils or other liquids will tend to migrate into and along a piece of wood by means of the capillaries in the wood grain. U.S. Pat. No. 2,241,167 (Storck) discloses this principle in connection with the absorbance of insect repellant by a wooden egg-shaped piece of cedar. The Storck device is also used to protect clothing from moth or other insect damage. It has no teachings with respect to air freshener devices.

Among the many continuous-action air freshener devices of the prior art are ceramic bowls. Some liquid air freshener is poured into each bowl through a top opening, which is then covered. The liquid gradually passes through the ceramic from the pool in the bowl and is evaporated at the surface of the bowl. The bowl has a relatively thin wall and encloses a large central chamber.

One problem with many types of continuous-action air freshener devices of the prior art is that it may be difficult to determine when the useful life of the product has ended. Usefulness often fades away with no readily perceptible sign.

OBJECTS OF THE INVENTION

It is an object of this invention to provide an air freshener where wood is used as the primary metering means for dispensing liquid air freshener.

Another object of this invention is to provide an attractive container for a reusable air freshener.

A further object of this invention is to provide a reusable air freshening device which indicates by a change in physical appearance whether or not it needs refilling.

Another object of this invention is to provide an air freshening device which prevents contact between the air freshening agent and other objects, so as to protect the surface of the object on which the device is placed and to prevent contact between the fragrance agent and clothing or other materials in the environment in which the device is used.

A further object of this invention is to provide an air freshening device which is resistant to breakage.

Another object of this invention is to provide an internal chamber which is of an ideal configuration to dispense the air freshener through the surface of the container.

Yet a further object of the invention is to provide an air freshening device which has no top cap or openings.

Still another object of the invention is to provide an air freshening device which can be made in various decorative shapes and sizes.

These and other important objects will be apparent from the following descriptions and from the drawings which follow.

SUMMARY OF THE INVENTION

The need for a refillable, attractive air freshening dispenser is fulfilled by the present invention which is a wooden member and a base member which are removably connected to each other. Liquid air freshening composition is loaded in an internal chamber in the wooden member and dispensed as a vapor on the outer surface of the wood. The device requires no top cap or openings for dispensing purposes and has a base member which functions both to seal off the chamber and to shield the surface on which the device sits from contact with the liquid fragrance agent or the wooden member. From all appearances, the device has no dispensing opening and appears to be simply a piece of decorative wood resting on a household surface.

The invention is based in part on the discovery that wood and, in particular, capillaries in the wood can act as a means for storing liquid air freshener and as a metering device for the vaporization of the freshener into the atmosphere. The capillaries rapidly absorb the liquid upon contact in the internal chamber of the wooden member and move the liquid through the member to the outer surface of the wood where, upon exposure to the atmosphere, the air freshener vaporizes. The invention is also partially based upon the discovery that as the liquid air freshener vaporizes, the wooden member loses its sheen and becomes lighter in color, thereby signaling the need for refilling the member with more air freshener.

The device includes a wooden member which has an orifice-free dispensing surface exposed to the atmosphere and which forms an internal chamber having an opening for receiving a liquid air freshening agent. The wooden member functions both as a container and a metering device for dispensal of the air freshener for substantially constant air freshening. The device also has means removably connected to the wooden member to close the opening in the member. In a preferred embodiment thereof, the removably connected means is made of plastic.

In one embodiment of the invention, the wooden member has a bottom surface which defines the opening. Contact between the member and a surface on which the device is placed is prevented by manufacturing the closing means from a material that is impermeable by the air freshening agent.

In a preferred embodiment of the invention, the wooden member is circumscribed by a lateral groove spaced above the bottom surface. The closing means may also have circumferentially-spaced, radially-inward projections arranged to engage this lateral groove. By inserting these projections into the groove, the closing means is thereby removably connected to the wooden member.

In another embodiment of the invention, the wooden member, when resting on the closing means, is symmetrical around a vertical axis which runs through the bottom surface thereof and the grain in the wooden member is substantially parallel to the vertical axis. The member may also have an outside surface which is configured such that wood end grain is distributed over substantial portions of the outside surface along the length of the device, thereby facilitating vaporization of the air freshening agent.

Additionally, the internal chamber of the member may have an annular configuration such that the chamber has a surface area in vertical alignment with the end grain distribution on the outside surface of the wood such an alignment thereby increases the chamber surface area and liquid absorption capability and facilitates the migration of the fragrance agent from the chamber to the outside surface.

The device is manufactured by shaping a block of wood on a lathe or by other means into a decorative shape to constitute the container for the fragrance agent. Any such shape must allow sufficient diameter in the main body of the wooden member to permit the hollowing out of a portion of the bottom of the wooden piece extending into the interior of the device in a preferably annular shape. In the preferred embodiment thereof, where the chamber formed is of an annular shape, the interaction of the oil in the chamber with the inside of the wood permits excellent dispersion of the liquid air freshener throughout the wood along the capillaries in the wood grain. The annular chamber may have vertical or sloping walls to facilitate migration of the fragrance agent along the wood capillaries.

The closing member is formed by molding it or by other similar means to a shape and size which will securely fit over the bottom of the wooden member. This closing member should ideally be of a sufficient size and shape to cover the opening to the fluid chamber and to adequately protect against contact between the air freshener surface and the surface of the table or other object on which the device is intended to rest as it accomplishes its air freshening purpose. Liquid air freshener in the desired scent is inserted into the interior chamber from the bottom of the wooden member and the closing member is then connected to the wooden member as it is held in a top-down position. The wooden member, with the closing means in place, is then righted and placed in the desired location on a table or other surface.

After filling the internal chamber with oil, the oil permeates the wood and migrates along the capillaries to the exterior wood surfaces. Upon exposure to the air, the oil vaporizes, resulting in the release of fragrance. The liquid air freshener is very quickly absorbed by the porous interior wood surfaces exposed to the oil, resulting in a substantially empty interior chamber during most normal use of the device. The preferably annular configuration of the internal chamber increases the chamber surface area and liquid absorption capability of the device. Since only some of the oil is exposed to the atmosphere at any one time, the wooden member acts as a metering device, thereby allowing the gradual and steady release of the fragrant oil vapor over time. Eventually, all of the oil is vaporized and the closing means may be removed by snapping it off or by some other detaching means. The internal chamber of the wooden member is then simply refilled in the same manner as previously indicated.

In the preferred embodiment of the device, the air freshening agent and the wood used to manufacture the wooden member are selected so that certain changes in physical appearance in the wooden member occur when release of the air freshening agent to the atmosphere approaches completeness, thereby indicating a need for refilling the chamber. These changes may include a loss of sheen in the wooden member or a lightening in the color of the member, or both, depending upon the wood and air freshener selected.

For example, as the oil is absorbed by the wood and migrates to the outside surfaces of the wooden member, the wood surfaces may take on a lustrous appearance or appear darker in color. However, as the oil evaporates and, if not replaced by additional oil migrating from the internal chamber, the exterior walls of the wooden member become dull in appearance and lighter in color. Therefore, by using wood as a container medium, one can rapidly and easily determine whether a refill of the air freshener is necessary by observing the changes in outside appearance of the wooden member.

Alternative embodiments of the invention contemplate the use of various decorative woods for wooden members in various shapes pleasing in appearance to the eye. Additionally, various liquid chamber shapes are possible although it is preferable to coordinate chamber shape and size with the desirable amount of exposure to internal wood surfaces to ensure the proper amount of continuous vaporization of the fragrance agent. Generally, this will be accomplished by the maximum exposure of the oils to the interior wood surfaces and wood grain capillaries.

The closing means may be composed of various types of impermeable materials, preferably plastic, and may also be of various sizes and shapes to suit the particular shape of the wooden member, so as to provide ease of removal and prevention of oil leakage. Various means of fixation of the closing means are also possible. However, the method should ideally allow for easy removal and reconnection to the wooden member.

DETAILED DESCRIPTIONS OF THE PREFERRED EMBODIMENTS

The present invention has the desirable characteristics of attractiveness in appearance, durability and reusability. A critical feature of the invention is the use of wood as a container for the air freshening agent to act as a metering device to dispense the oil through the surface of the wood. Furthermore, the invention satisfies environmental concerns and provides a means to easily determine from the appearance of the outside of the wooden member whether the chamber needs to be refilled. The invention also incorporates a protective base as a closing means which prevents spillage of the liquid fragrance agent from the internal chamber and protects the surfaces of the objects which come in contact with the air freshener device.

Figure 1:
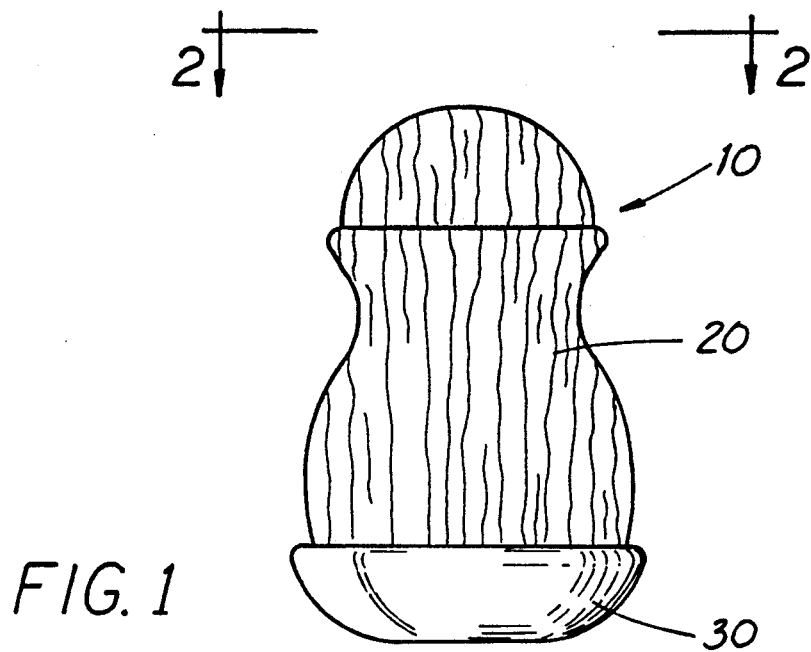
FIG. 1 is a side view of the air freshener with closing means in place, showing the grain of the wood.
Figure 2:
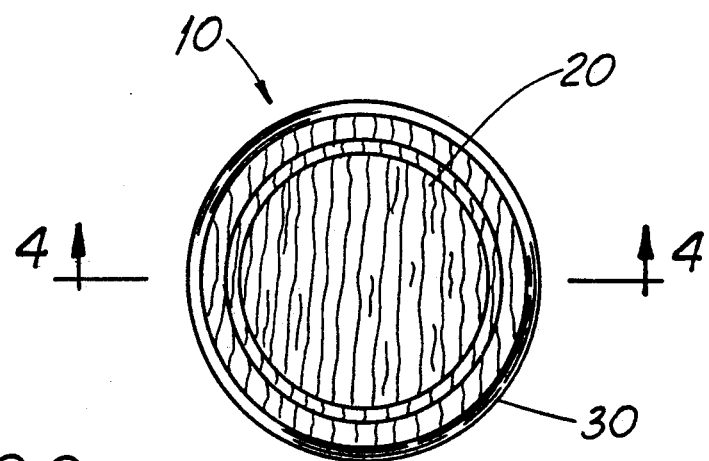
FIG. 2 is a top view of the air freshener with closing means in place.

The preferred embodiment of the invention 10 is an attractively shaped wooden member 20, to which is removably connected a closing means 30, preferably made of plastic, which securely fits over the lower portion of the wooden member 20 and snaps into place in the configuration depicted in FIG. 1. The closing means 30 surrounds the entire perimeter of the wooden member 20, as depicted in FIG. 2.

Figure 3:
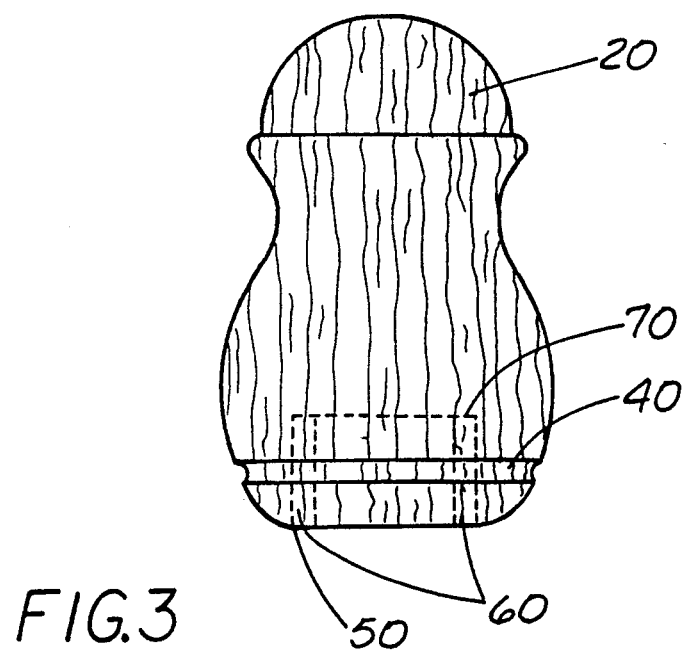
FIG. 3 is a side view of the air freshener without the closing means in place, showing the fragrance loading chamber in phantom lines.
Figure 4:
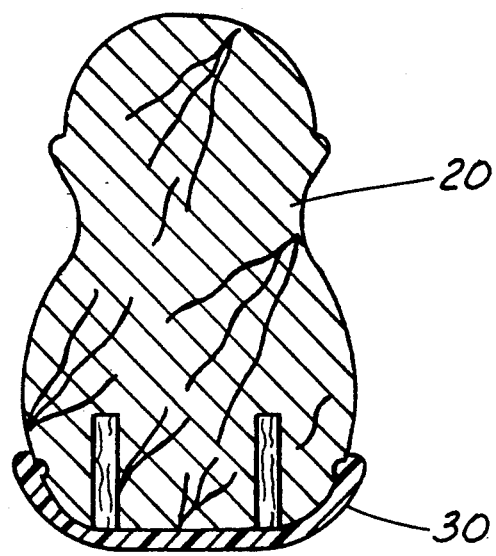
FIG. 4 is a cutaway view of the air freshener in the position depicted in FIG. 1 along the lines 4—4, as depicted in FIG. 2.

FIG. 3 depicts the wooden member 20 only, which incorporates a groove 40 surrounding the perimeter of the lower portion of the wooden member 20 at a latitude slightly elevated from the bottom 50. In the preferred embodiment, as depicted in FIG. 3, an annular cavity 60 is cut from the bottom 50 of the wooden member 20, which cavity 60 extends into the interior of the wooden member 20 to the extent desirable to maintain structural strength while maximizing the size of the interior chamber walls 70. This configuration tends to maximize contact between the fragrance agent and interior wood surface. The chamber 60 is depicted in FIG. 3 with phantom lines.

Figure 5:
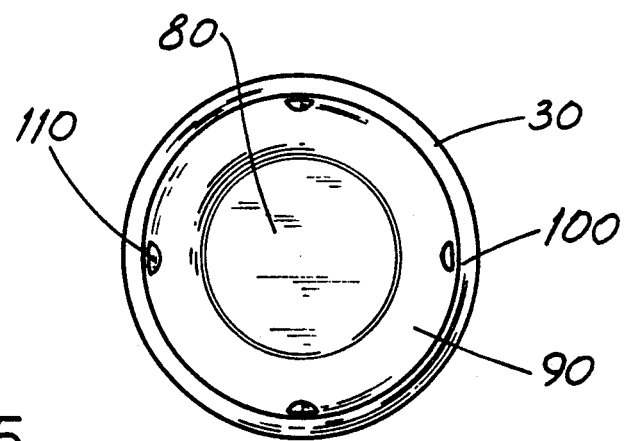
FIG. 5 is a top view of the closing means only.

The closing means 30 is made of plastic or other impermeable material and is molded or formed by other means into the shape depicted in FIG. 5. The closing means 30 has a flat surface 80 slightly larger in diameter than the bottom 50 of the wooden member 20 and upraised sides 90 of slightly greater dimensions, but of the same shape as the sides of the wooden member 20.

On the top of the upraised sides 90 of the closing means 30 is a narrow rim 100 which contains four projections 110, equidistantly located from one another and each projecting toward the center axis of the closing means 30, assuming the axis is projected through the center. Each projection 110 is designed in size and location to fit securely into the groove 40 surrounding the perimeter of the wooden member 20. When the closing means 30 is placed over the bottom 50 of the wooden member 20, the projections 110 on the closing means 30 snap into the groove 40 on the wooden member 20 and hold the closing means 30 in place firmly on the wooden member 20.

Figure 6:
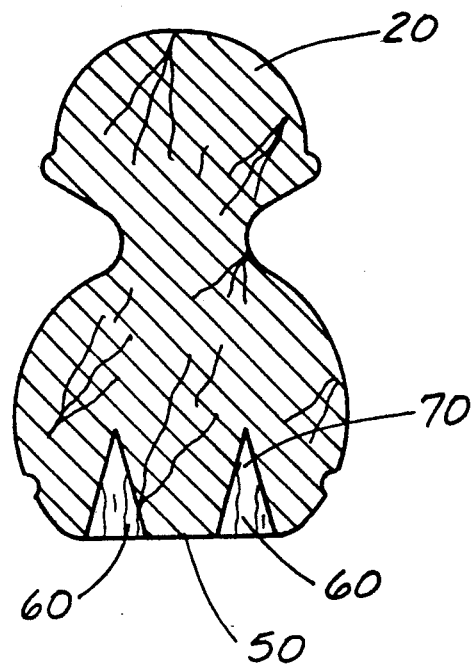
FIG. 6 is a cross-sectional view of the air freshener without the closing means in place, showing an annular fragrance loading chamber with sloping walls.
Figure 7:
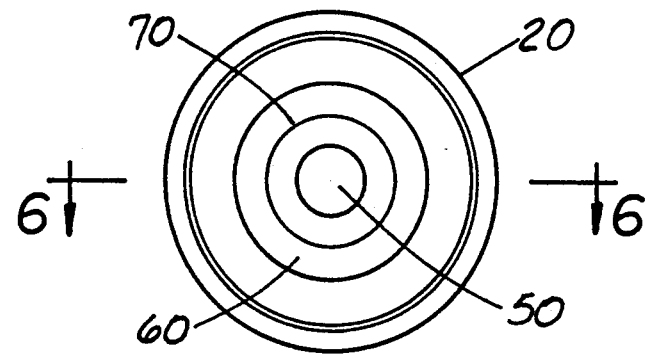
FIG. 7 is a bottom view of the entire air freshener depicted in FIG. 6 in cross-section.

FIGS. 6 and 7 depict two views of the air-freshener without closing means in place having an alternate V-shaped configuration to the annular loading chamber, which may further facilitate upwardly migration of the freshening agent through the wood capillaries.

The air freshener 10 is used by first removing the closing means 30 from the wooden member 20. The fragrance agent is then poured into the chamber 60 while the wooden member 20 is held in a position with the bottom 50 pointing in an upwardly direction. The closing means 30 is then snapped onto the bottom 50 of the wooden member 20, thereby sealing off the chamber 60. The device 10 is then inverted to an upright position and placed in the desired location for use. As the fragrant oils come into contact with the interior wood surfaces of the chamber 70, they are absorbed by the wood and migrate along the capillaries of the wood through the grain thereof until reaching the outside of the wooden member 20.

Upon contact with the air, the oil vaporizes, thereby emitting the fragrance into the air. As oil reaching the surface of the wooden member 20 vaporizes, additional oil below the surface moves into its place and thereafter undergoes the same vaporization until the reservoir of oil in the chamber 60 is depleted. The oil is initially absorbed by the wooden member 20 from the chamber 60 fairly rapidly and then travels in a slow and regular fashion through the wood grain capillaries. Wooden member 20 acts as a metering device, resulting in a continuous and regular flow of oil outwardly from the inner chamber 60 to the outer surface of the wooden member 20.

As the wood absorbs the oil, it takes on a lustrous and darker appearance, making the wooden member 20 very attractive. When the oil is completely vaporized, the wooden member 20 loses its sheen and lightens in color, thereby indicating that refilling is necessary.

The wooden member 20 is refilled by turning it so that the bottom 50 faces in an upwardly direction and removing the closing means 30 by snapping it off of the bottom 50. Liquid fragrance agent is then poured into the chamber 60 and the closing means 30 is then snapped back into place. The air freshener 10 is then returned to its upright position in its former location or such other site as is desirable.

Any wood may be used for the wooden member 20 but regardless of the wood chosen, the preferred embodiment would require that the grain of the wood run in a vertical direction along the upright axis of the wooden member 20 to enhance the release of the fragrance in an upwardly direction. The closing means 30 may be manufactured from any impermeable substance, although a heavy-duty plastic would be preferable.

The method of affixation of the closing means 30 to the wooden member 20 may also vary. For example, instead of a groove 40 surrounding the perimeter of the wooden member 20, lateral grooves appropriately placed to accommodate the projections 110 on the closing means 30 would accomplish the same purpose of holding the closing means 30 firmly in place on the wooden member 20.

While the principles of this invention have been described in connection with specific embodiments, it should be clearly understood that these descriptions are made only by way of example and are not intended to limit the scope of the invention.

I claim:

1. An air freshening device comprising:
   a wooden member having a solid body forming an orifice-free wooden outside dispensing surface exposed to the atmosphere and an inside receiving surface defining an internal loading chamber for receiving a liquid air freshening agent for transitory absorption for containment in the solid body for dispensing therefrom throughout the dispensing cycle, the chamber having an opening after charging and recharging; and
   means removably connected to the wooden member to close the opening;
   whereby the wooden member solid body itself functions as a rechargeable container and metering device for substantially constant air freshening.

2. The device of claim 1 wherein:
   the wooden member has a bottom surface which defines the opening; and
   the closing means is of a material impermeable by the air freshening agent such that contact between the wooden member and a surface on which the device is placed is prevented;
   whereby the closing means serves dual purposes of facilitating use and reuse and of protecting against surface degradation from the air freshening agent.

3. The device of claim 2 wherein:
   the wooden member, when resting on the closing means, is symmetrical around a vertical axis which runs through the bottom surface; and
   the wooden member has a grain substantially parallel to the vertical axis.

4. The device of claim 3 wherein the wooden member has an outside surface configured such that wood end grain is distributed over substantial portions of the outside surface along the length of the device, thereby to facilitate vaporization of the air freshening agent.

5. The device of claim 4 wherein the internal chamber has an annular configuration such that the chamber has surface area in vertical alignment with said substantial portions of the outside surface, thereby to increase the chamber surface area and liquid absorption capability and facilitate migration from the chamber to the outside surface.

6. The device of claim 2 wherein:
   the wooden member is circumscribed by a lateral groove spaced above the bottom surface; and
   the closing means includes circumferentially-spaced, radially-inward projections arranged to engage the lateral groove,
   whereby the closing means is removably connected to the wooden member by insertion of the projections into the groove.

7. The device of claim 2 wherein the closing means is of a plastic material.

8. The device of claim 1 wherein the air freshening agent and the wood for the wooden member are selected such that the wooden member changes in physical appearance when release of the air freshening agent to the atmosphere approaches completeness, thereby indicating a need for refilling the chamber.

9. The device of claim 8 wherein the change in physical appearance is a loss of sheen in the member.

10. The device of claim 8 wherein the change in physical appearance is a lightening in color of the member.

11. The device of claim 1 wherein the internal chamber has an annular configuration, thereby to increase the chamber surface area and liquid absorption capability.

12. The device of claim 11 wherein the internal chamber has sloping walls to thereby facilitate migration of the air freshening agent through the capillaries.

13. The device of claim 1 wherein the air freshening agent is absorbed within the wooden member and the chamber is substantially free of liquid.

14. An air freshening device comprising:
   a wooden member having an orifice-free dispensing surface exposed to the atmosphere and forming an internal chamber for receiving a liquid air freshening agent, the wooden member having a bottom surface defining an opening to the chamber;
   means removably connected to the wooden member to close the opening, the closing means being of a material impermeable by the air freshening agent such that contact between the wooden member and a surface on which the device is placed is prevented; and
   the wooden member being circumscribed by a lateral groove spaced above the bottom surface and the closing means including circumferentially-spaced, radially-inward projections arranged to engage the lateral groove, such that the closing means is removably connected to the wooden member by insertion of the projections into the groove;

whereby the wooden member functions as both a container and a metering device for substantially constant air freshening.

15. An air freshening device comprising:
a wooden member having an orifice-free dispensing surface exposed to the atmosphere and forming an internal chamber for receiving a liquid air freshening agent, the wooden member having a bottom surface defining an opening to the chamber;
means removably connected to the wooden member to close the opening, the closing means being of a material impermeable by the air freshening agent such that contact between the wooden member and a surface on which the device is placed is prevented;
the wooden member, when resting on the closing means, being symmetrical around a vertical axis which runs through the bottom surface and having a grain substantially parallel to the vertical axis and an outside surface configured such that wood end grain is distributed over substantial portions of the outside surface along the length of the device to facilitate vaporization of the air freshening agent; and
the internal chamber having an annular configuration such that the chamber has surface are in vertical alignment with said substantial portions of the outside surface, thereby to increase the chamber surface area and liquid absorption capability and facilitate migration from the chamber to the outside surface;
whereby the wooden member functions as both a container and a metering device for substantially constant air freshening.

16. An air freshening device comprising:
a wooden member having an orifice-free dispensing surface exposed to the atmosphere and forming an internal chamber for receiving a liquid air freshening agent, the chamber having an opening and an annular internal configuration thereby to increase the chamber surface area and liquid absorption capability; and
means removably connected to the wooden member to close the opening;
whereby the wooden member functions as both a container and a metering device for substantially constant air freshening.

17. The device of claim 16 wherein the internal chamber has sloping walls to thereby facilitate migration of the air freshening agent through the capillaries.

18. An air freshening device comprising:
a wooden member having an orifice-free dispensing surface exposed to the atmosphere and forming an internal chamber for receiving a liquid air freshening agent, the chamber having an opening, and the air freshening agent and the wood for the wooden member being selected such that the wooden member changes in physical appearance when release of the air freshening agent to the atmosphere approaches completeness, thereby indicating a need for refilling the chamber; and
means removably connected to the wooden member to close the opening;
whereby the wooden member functions as both a container and a metering device for substantially constant air freshening.

19. The device of claim 18 wherein the change in physical appearance is a loss of sheen in the member.

20. The device of claim 18 wherein the change in physical appearance is a lightening in color of the member.

* * * * *

UNITED STATES PATENT AND TRADEMARK OFFICE
CERTIFICATE OF CORRECTION

PATENT NO. : 5,259,555
DATED : November 9, 1993
INVENTOR(S) : Bruce C. Kiefer

It is certified that error appears in the above-identified patent and that said Letters Patent is hereby corrected as shown below:

On the Title Page, Item [57]:
In the Abstract, line 6, after "is" insert --placed--.

In claim 15, line 23, change "are" to --area--.

Signed and Sealed this

Nineteenth Day of April, 1994

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO. : 5,259,555
DATED : November 9, 1993
INVENTOR(S) : Bruce C. Kiefer

It is certified that error appears in the above-indentified patent and that said Letters Patent is hereby corrected as shown below:

Column 7,
in claim 1, lines 9 and 10, delete "after charging and recharging". and Line 12 of claim 1, after "opening" insert --after charging and recharging--.

Signed and Sealed this

Twenty-ninth Day of November, 1994

Attest:

BRUCE LEHMAN

*Attesting Officer*         *Commissioner of Patents and Trademarks*